United States Patent [19]
Cheruvallath et al.

[11] Patent Number: 5,959,099
[45] Date of Patent: *Sep. 28, 1999

[54] PROTECTING GROUP FOR SYNTHESIZING OLIGONUCLEOTIDE ANALOGS

[75] Inventors: Zacharia S. Cheruvallath; Daniel C. Capaldi, both of San Diego; Vasulinga T. Ravikumar, Carlsbad; Douglas L. Cole, San Diego, all of Calif.

[73] Assignee: ISIS Pharmaceuticals, Inc., Carlsbad, Calif.

[*] Notice: This patent is subject to a terminal disclaimer.

[21] Appl. No.: 09/103,399

[22] Filed: Jun. 24, 1998

Related U.S. Application Data

[60] Continuation of application No. 08/933,133, Sep. 18, 1997, Pat. No. 5,783,690, which is a division of application No. 08/811,232, Mar. 3, 1997, Pat. No. 5,760,209.

[51] Int. Cl.⁶ .................................................. C07H 19/04
[52] U.S. Cl. ................... 536/26.1; 536/22.1; 536/24.5; 536/25.34
[58] Field of Search ................... 536/26.1, 24.5, 536/25.34, 55.3, 22.1

[56] References Cited

U.S. PATENT DOCUMENTS

| Re. 34,069 | 9/1992 | Köster et al. . |
| 3,923,763 | 12/1975 | Edmonson ............................ 526/221 |
| 4,310,662 | 1/1982 | Crea . |
| 4,373,071 | 2/1983 | Itakura . |
| 4,401,796 | 8/1983 | Itakura . |
| 4,415,732 | 11/1983 | Caruthers et al. . |
| 4,419,509 | 12/1983 | Hsiung . |
| 4,458,066 | 7/1984 | Caruthers et al. . |
| 4,500,707 | 2/1985 | Caruthers et al. . |
| 4,522,735 | 6/1985 | Chasar . |
| 4,668,777 | 5/1987 | Caruthers et al. . |
| 4,689,405 | 8/1987 | Frank et al. . |
| 4,725,677 | 2/1988 | Köster et al. . |
| 4,816,571 | 3/1989 | Andrus et al. . |
| 4,965,349 | 10/1990 | Woo et al. . |
| 4,973,679 | 11/1990 | Caruthers et al. . |
| 5,003,097 | 3/1991 | Beaucage et al. . |
| 5,071,974 | 12/1991 | Groody . |
| 5,132,418 | 7/1992 | Caruthers et al. . |
| 5,151,510 | 9/1992 | Stec et al. . |
| 5,166,387 | 11/1992 | Hirschbein . |
| 5,218,088 | 6/1993 | Gorenstein et al. . |
| 5,218,103 | 6/1993 | Caruthers et al. . |
| 5,252,723 | 10/1993 | Bhatt . |
| 5,252,760 | 10/1993 | Urdea et al. . |
| 5,264,566 | 11/1993 | Froehler et al. ..................... 536/25.34 |
| 5,292,875 | 3/1994 | Stec et al. . |
| 5,310,894 | 5/1994 | Zeiger . |
| 5,359,051 | 10/1994 | Cook et al. . |
| 5,359,052 | 10/1994 | Stec et al. . |
| 5,401,837 | 3/1995 | Nelson . |
| 5,436,327 | 7/1995 | Southern et al. . |
| 5,449,769 | 9/1995 | Bhatt . |
| 5,510,239 | 4/1996 | Baracchini, Jr. et al. . |
| 5,510,476 | 4/1996 | Ravikumar et al. . |
| 5,512,438 | 4/1996 | Ecker . |
| 5,512,668 | 4/1996 | Stec et al. . |
| 5,514,788 | 5/1996 | Bennett et al. . |
| 5,514,789 | 5/1996 | Kempe . |
| 5,523,389 | 6/1996 | Ecker et al. . |
| 5,571,902 | 11/1996 | Ravikumar et al. . |
| 5,614,621 | 3/1997 | Ravikumar et al. . |
| 5,760,209 | 6/1998 | Cheruvallath et al. ................. 536/55.3 |
| 5,783,690 | 7/1998 | Cheruvallath et al. ............. 536/25.34 |

FOREIGN PATENT DOCUMENTS

| 8902521 | 5/1991 | Niger . |
| WO 94/15946 | 7/1994 | WIPO . |
| WO 95/04065 | 2/1995 | WIPO . |
| WO 95/32980 | 12/1995 | WIPO . |
| WO 96/09406 | 3/1996 | WIPO . |
| WO 97/19092 | 5/1997 | WIPO . |

OTHER PUBLICATIONS

H.C.P.F. Roelen et al., "A Study on the Use of Phenylacetyl Disulfide in the Solid–Phase Synthesis of Oligodeoxynucleoside Phosphorothioates", Recl. Trav. Chim. Pays–Bas, vol. 110, pp. 325–331, (1991).

George Barany et al., "A General Strategy for Elaboration of the Dithiocarbonyl Functionality, –(C=O)SS–: Application to the Synthesis of Bis(Chlorocarbonyl)Disulfane and Related Derivatives of Thiocarbonic Acids", J. Org. Chem., vol. 48, pp. 4750–4761, (1983).

Mitsuo Kodamari et al., "A Convenient Synthesis of Bis(Acyl) Disulfides Using Phase–Transfer Catalysis", Synthesis, Aug. (1981), pp. 637–638.

(List continued on next page.)

Primary Examiner—Gary L. Kunz
Attorney, Agent, or Firm—Oblon, Spivak, McClelland, Maier & Neustadt, P.C.

[57] ABSTRACT

A 2-N-amidoethyl protected nucleoside analog phosphoramidite of formula (1):

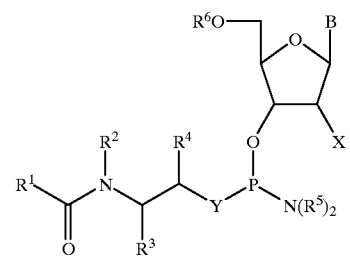

(1)

is useful in the synthesis of a wide variety of oligonucleotide analogs. Coupling yields with phosphoramidite (1) in solution or solid phase oligonucleotide analog synthesis are high and the 2-N-amidoethyl protecting group can be removed easily under standard conditions.

22 Claims, No Drawings

OTHER PUBLICATIONS

P.C.J. Kamer et al., "An Efficient Approach Toward the Synthesis of Phosphorothioate Diesters Via the Schönberg Reaction", Tetrahedron Letters, vol. 30, No. 48, pp. 6757–6760, (1989).

Radhakrishnan P. Iyer et al., "A Novel Nucleoside Phosphoramidite Synthon Derived from 1R,2S–Ephedrine", Tetrahedron: Asymmetry, vol. 6, No. 5, pp. 1051–1054, (1995).

Kazunobu Miura et al., "Blockwise Mechanical Synthesis of Oligonucleotides by the Phosphoramidite Method", Chem. Pharm. Bull, vol. 35, No. 2, pp. 833–836, (1987).

Willi Bannwarth, "Synthesis of Oligodeoxynucleotides by the Phosphite–Triester Method Using Dimer Units and Different Phosphorous–Protecting Groups", Helvetica Chimica Acta, vol. 68, pp. 1907–1913, (1985).

G. Kumar et al., "Improvements in Oligodeoxyribonucleotide Synthesis: Methyl N,N–Dialkylphosphoramidite Dimer Units for Solid Support Phosphite", J. Org. Chem., vol. 49, pp. 4905–4912, (1984).

Radhakrishnan P. Iyer et al., "Nucleoside Oxazaphospholidines as Novel Synthons in Oligonucleotide Synthesis", J. Org. Chem., vol. 60, No. 17, pp. 5388–5389, (1995).

Wakamiya et al., Chem. Abstr. 176265, vol. 99, Bull. Chem. Soc., Jpn. 56 (7): 2044–9, 1983.

Hasegawa et al., Chem. Abstr. 175252, vol. 100, Carbo Res. 123(2): 183–199, 1983.

Zhang et al, "Syntheses and properties of novel thiono triester modified antisense oligodeoxynucleotide phosphorothiotes", Bioorganic & Medicinal Chem., vol. 5, No. 15, pp. 1735–1740, Aug. 3, 1995.

Zhang et al, "Thiono triester modified antisense oligonucleotides for inhibition of human cytomegalovirus in vitro", Bioorganic & Medicinal Chem., vol. 16, pp. 1911–1916, Aug. 20, 1996.

Schroll et al, "Novel symmetrical and mixed carbamoyl and amino polysulfanes by reactions of (alkoxydichloromethyl) polysulfanyl substrates with n–methylaniline", J. Org. Chem., vol. 51, No. 10, pp. 1866–1881, 1986.

Bokarev et al, "Synthesis of BIS(alkyl xanthyl) trisulfides", Chem Abstracts, vol. 62, No. 7., col. 7631, see Abstract No. 7631c.

PROTECTING GROUP FOR SYNTHESIZING OLIGONUCLEOTIDE ANALOGS

This application is a Continuation of application Ser. No. 08/933.133. filed on Sep. 18, 1997, now U.S. Pat. No. 5,783,690 which is a divisional of application Ser. No. 08/811.232 filed on Mar. 3, 1997, now U.S. Pat. No. 5,760,209.

BACKGROUND OF THE INVENTION

1. Field of the Invention

The present invention is directed to a novel protecting group useful in the synthesis of oligonucleotide analogs.

2. Discussion of the Background

It is well-known that most of the bodily states in mammals, including most disease states, are effected by proteins. By acting directly or through their enzymatic functions, proteins contribute in major proportion to many diseases in animals and man.

Classical therapeutics has generally focused on interactions with such proteins in an effort to moderate their disease causing or disease potentiating functions. Recently, however, attempts have been made to directly inhibit the production of proteins involved in disease by interacting with the messenger RNA (mRNA) molecules that direct their synthesis. These interactions have involved the hybridization of complementary, or antisense, oligonucleotides or oligonucleotide analogs to MRNA. Hybridization is the sequence-specific hydrogen bonding of an oligonucleotide or oligonucleotide analog to an MRNA sequence via Watson-Crick hydrogen bond formation. By interfering with the production of proteins involved in disease, it has been hoped to effect therapeutic results with maximum effect and minimal side effects.

The pharmacological activity of antisense oligonucleotides and oligonucleotide analogs depends on a number of factors that influence the effective concentration of these agents at specific intracellular targets. One important factor for oligonucleotides and analogs thereof is their stability to nucleases. It is unlikely that unmodified oligonucleotides containing phosphodiester linkages will be useful therapeutic agents because they are rapidly degraded by nucleases. Modified oligonucleotides which are nuclease resistant are therefore greatly desired.

Phosphorothioate and phosphorodithioate oligonucleotide analogs have one or both of the non-bridging oxygens of the natural phosphodiester linkage replaced with sulphur, respectively, are especially promising antisense therapeutics. These oligonucleotide analogs are highly resistant to nucleases, have the same charge as natural phosphodiester-containing oligonucleotides, and are taken up by cells in therapeutically effective amounts. Other promising oligonucleotide analogs are those containing a mixture of phosphodiester and phosphorothioate and/or phosphorodithioate linkages. For a description of sulfurized oligonucleotide analogs see, Baracchini et al, U.S. Pat. No. 5,510,239; Ecker, U.S. Pat. No. 5,512,438; Bennett et al, U.S. Pat. No. 5,514,788; and Ecker et al, U.S. Pat. No. 5,523,389.

Oligonucleotide analogs are conveniently synthesized with automated DNA synthesizers using phosphoramidite chemistry. This is a highly efficient approach to the synthesis of oligonucleotide analogs, with coupling yields typically greater than 99%.

A more recent method for the synthesis of oligonucleotide analogs is the "blockmer" approach. In blockmer synthesis, an oligonucleotide analog is made by the sequential coupling of short protected oligomers or blocks, e.g., a dinucleotide, on a solid support. This strategy offers several advantages over the conventional synthetic approach which involves the sequential coupling of monomeric nucleoside phosphoramidites. The number of synthesis cycles required to prepare an oligonucleotide analog is reduced, saving time and minimizing reagent consumption. Importantly, the blocks may be prepared on a large scale using inexpensive solution phase synthesis techniques. The blockmer approach is described in the following references: Ravikumar et al, WO 95/32980; WO 94/15947; *Journal of organic Chemistry* 1984, 49, 4905–4912; *Helevetica Chimica Acta* 1985, 68, 1907–1913; *Chem. Pharm. Bull.* 1987, 35, 833–836.

One of the most important elements of oligonucleotide analog synthesis is the selection of a protecting group for the internucleosidic phosphorous linkages during step-wise synthesis. Removal of this protecting group should be fast and proceed through a mechanism which avoids nucleophilic attack at the phosphorous atom, which would result in chain scission. In addition, protected phosphoramidite monomers should be easy to synthesize inexpensively on a large scale. Phosphoramidite monomers containing the most widely-used phosphorous protecting group, β-cyanoethyl, are very expensive to produce on a large scale. In addition, the phosphitylating reagent used in preparing β-cyanoethyl protected phosphoramidites is explosive, which further limits the use of this protecting group in large scale synthesis. It is therefore of prime importance to develop low-cost protected nucleoside analog phosphoramidites which couple efficiently (>99%) during step-wise synthesis and may be deprotected quickly in high yield under standard conditions.

SUMMARY OF THE INVENTION

It is an object of the present invention to provide a protected nucleoside analog phosphoramidite which may be prepared inexpensively and safely on a large scale.

It is another object of the present invention to provide a protected nucleoside analog phosphoramidite which couples efficiently in step-wise oligonucleotide analog synthesis.

It is another object of the present invention to provide a protected nucleoside analog phosphoramidite which may be deprotected in high yield following step-wise oligonucleotide analog synthesis.

It is an object of the present invention to provide a protected dinucleotide analog phosphoramidite which may be prepared inexpensively and safely on a large scale.

It is another object of the present invention to provide a protected dinucleotide analog phosphoramidite which couples efficiently in step-wise oligonucleotide analog synthesis.

It is another object of the present invention to provide a protected dinucleotide analog phosphoramidite which may be deprotected in high yield following step-wise oligonucleotide analog synthesis.

It is another object of the present invention to provide synthetic intermediates for the synthesis of the nucleoside and dinucleotide phosphoramidites described above.

It is another object to provide a protected oligonucleotide analog that may be deprotected in high yield by treatment with a base.

It is another object of the present invention to provide a method of synthesizing an oligonucleotide analog using the protected nucleoside analog phosphoramidite provided by the present invention.

These objects and others may be accomplished with a 2-Namidoethyl protected nucleoside analog phosphoramidite of formula (1):

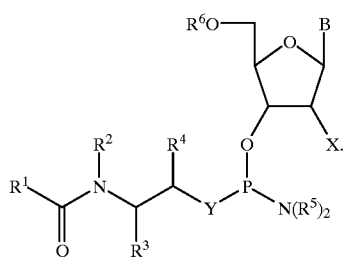
(1)

The above objects may also be accomplished with a 2-N-amidoethyl protected dinucleotide analog phosphoramidite of formula (5):

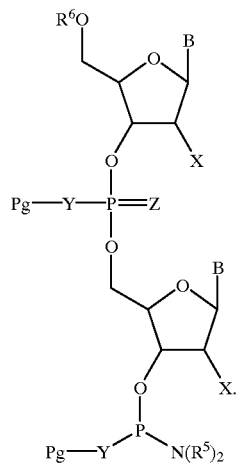
(5)

The above objects may also be accomplished with 2-Namidoethyl protected oligonucleotide analog of formula (11):

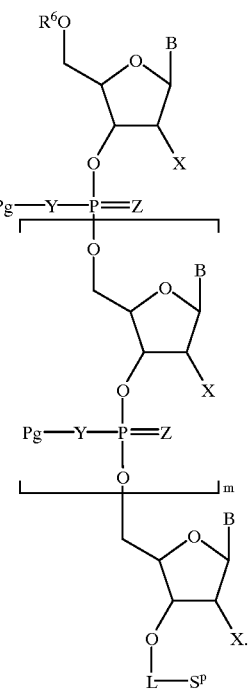
(11)

The above objects may also be accomplished with a phosphitylating reagent of formula (3):

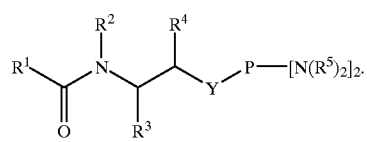
(3)

The above objects may also be accomplished by a method of synthesizing the 2-N-amidoethyl protected nucleoside analog phosphoramidite of formula (1) by reacting a blocked nucleoside analog of formula (4):

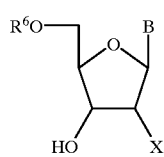
(4)

with the phosphitylating agent of formula (3) to produce the nucleoside analog phosphoramidite (1).

The above objects may also be accomplished by a method of synthesizing the 2-N-amidoethyl protected dinucleotide analog phosphoramidite of formula (5) by reacting a blocked dinucleotide analog of formula (10):

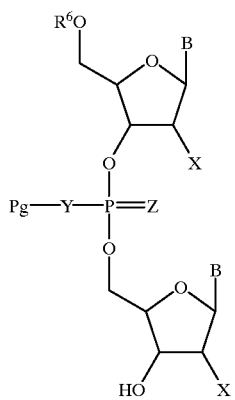

(10)

with a phosphitylating reagent having the formula Pg—Y—P—[N($R^5$)$_2$]$_2$ to produce the dinucleotide analog phosphoramidite of formula (5).

The above objects may also be accomplished with a method of synthesizing the 2-N-amidoethyl protected oligonucleotide analog of formula (11), by:

(a) providing a protected nucleoside analog of formula (12), which is attached to a solid support and contains a blocked 5' hydroxyl group:

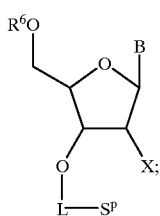

(12)

(b) deblocking the blocked hydroxyl group to produce a nucleoside analog attached to a solid support having a free 5' hydroxyl group;

(c) reacting the free 5' hydroxyl group with a nucleoside analog phosphoramidite of formula (6) having a blocked 5' hydroxyl group to produce an oligonucleotide analog containing a phosphorous(III) linkage and a blocked 5' hydroxyl group

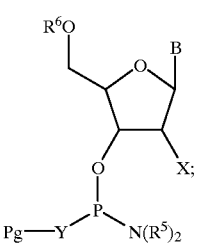

(6)

(d) reacting the phosphorous(III) linkage with an oxidizing agent or a sulfurizing reagent to produce an oligonucleotide analog containing an oxidized or sulfurized phosphorous(V) linkage and a blocked 5' hydroxyl group; and (e) optionally, repeating steps (b) through (d) at least once to produce 2-N-amidoethyl protected oligonucleotide analog (11).

The above objects may also be accomplished by a method of synthesizing an oligonucleotide analog by simultaneously deprotecting and removing the 2-N-amidoethyl protected oligonucleotide analog of formula (11) from a solid support to produce a deprotected oligonucleotide analog of formula (13):

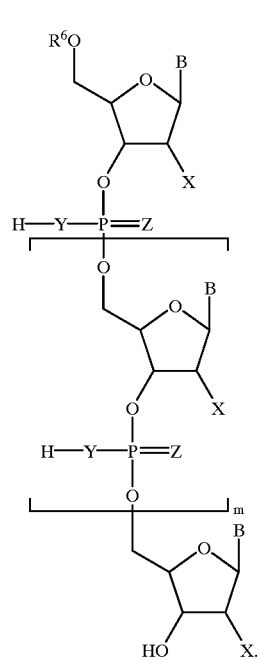

(13)

The above objects may also be accomplished by a method of synthesizing a phosphitylating reagent of formula (3) by reacting an amide having the formula $R^1CONR^2CHR^3CHR^4$—YH with a phosphorous trihalide in the presence of an amine having the formula HN ($R^5$)$_2$ to produce the phosphitylating reagent (3).

DETAILED DESCRIPTION OF THE INVENTION

A more complete appreciation of the invention and many of the attendant advantages thereof will be readily obtained as the same becomes better understood by reference to the following detailed description.

The present invention is directed to a 2-N-amidoethyl protected nucleoside analog phosphoramidite of formula (1):

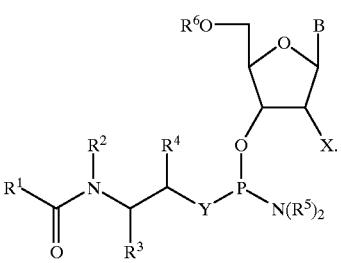

(1)

Nucleoside analog phosphoramidite (1) is useful in the synthesis of a wide variety of oligonucleotide analogs. Coupling yields with phosphoramidite (1) in solution or solid phase oligonucleotide analog synthesis are high, and the 2-N-amidoethyl protecting group may be removed easily under standard conditions. Further, the synthesis of nucleoside phosphoramidite (1) avoids many of the problems associated with the preparation of β-cyanoethyl protected phosphoramidites.

As used in the present invention, the term "oligonucleotide analog" includes linear oligomers of natural or modified nucleosides linked by phosphodiester bonds or analogs thereof ranging in size from a few monomeric units, e.g., two or three, to several hundred monomeric units. Oligonucleotide analogs include modifications of the heterocyclic base moiety and/or the sugar portion of a component nucleotide. In particular, the term includes non-natural oligomers containing phosphorus(V) linkages which are sulfurized. Preferably, the modifications do not inhibit the ability of an oligonucleotide analog to hybridize with a target nucleic acid. The term "nucleoside analog" refers to a natural or modified nucleoside. In particular, this term includes nucleosides that are modified at the heterocyclic base and/or sugar to enhance hybridization to the target nucleic acid. It is to be understood that the stereochemical relationship between the sugar substituents in the nucleoside and oligonucleotide analogs disclosed herein is preferably the same as that of naturally-occurring DNA and RNA, see G. M. Blackburn and M. J. Gait (eds.), *Nucleic Acids in Chemistry and Biology* (ILR Press, 1990), Chapter 2, pp. 19–70.

The term "2-N-amidoethyl group" refers to the group having the formula $R^1CONR^2CHR^3CHR^4$—. Preferably, $R^1$ is a group that permits the 2-N-amidoethyl group to be removed by treatment with a base and/or a nucleophile, preferably 20–30 wt % aqueous ammonium hydroxide. Preferably, $R^1$ is $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. The term "$C_1$–$C_8$ alkyl" includes linear, branched and cyclic alkyl groups. The term "substituted" means that up to three hydrogen atoms in the group are substituted with up to three halogen, nitro, cyano, $C_1$–$C_8$ alkyl, O-$C_1$–$C_8$ alkyl, N-$C_1$–$C_8$ alkyl, S-$C_1$–$C_8$ alkyl groups or combinations thereof. More preferably, $R^1$ is $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms or substituted $C_3$–$C_{11}$ hetaryl containing up to three heteroatoms. Even more preferably, $R^1$ is methyl, fluoromethyl, difluoromethyl or trifluoromethyl. Most preferably, $R^1$ is methyl, trifluoromethyl or phenyl.

The nitrogen atom of the 2-N-amidoethyl group may be unsubstituted, i.e., $R^2$ may be hydrogen, or substituted. Preferably, $R^2$ is hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. More preferably, $R^2$ is hydrogen or $C_1$–$C_8$ alkyl. Most preferably, $R^2$ is hydrogen or methyl.

The ethyl moiety of the 2-N-amidoethyl group may be unsubstituted, e.g., $R^3$ and $R^4$ may both be hydrogen. Alternatively, the ethyl moiety may be substituted with groups that preferably do not compromise the stability of the 2-N-amidoethyl group during oligonucleotide analog synthesis and permit the protecting group to be removed by treatment with a base and/or a nucleophile following stepwise assembly of an oligonucleotide analog. Preferable $R^3$ and $R^4$ groups are hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. More preferably, $R^3$ is hydrogen or linear $C_1$–$C_8$ alkyl. Most preferably, $R^3$ is hydrogen or methyl. More preferably, $R^4$ is hydrogen, $C_6$–$C_{14}$ aryl, substituted $C_6$–$C_{14}$ aryl, $C_3$–$C_{11}$ hetaryl containing up to three heteroatoms or substituted $C_3$–$C_{11}$ hetaryl containing up to three heteroatoms. Most preferably, $R^4$ is hydrogen or phenyl. The $R^3$ and $R^4$ groups are independently selected, i.e., they may be the same or different.

Alternatively, $R^3$ and $R^4$, together with the carbon atoms they are bonded to, may form a $C_3$–$C_8$ cycloalkyl group, a substituted $C_3$–$C_8$ cycloalkyl group, a $C_2$–$C_8$ heterocycloalkyl group containing up to three heteroatoms or a substituted $C_2$–$C_8$ heterocycloalkyl group containing up to three heteroatoms. In this embodiment, $R^3$ and $R^4$, together with the carbon atoms they are bonded to, preferably form a $C_3$–$C_8$ cycloalkyl group or a substituted $C_3$–$C_8$ cycloalkyl group. More preferred cycloalkyl groups are $C_4$–$C_7$ or substituted $C_4$–$C_7$ groups, with $C_5$–$C_6$ or substituted $C_5$–$C_6$ groups most preferred. An unsubstituted cycloalkyl group is particularly preferred. An unsubstituted $C_6$ cycloalkyl group is most particularly preferred. The stereochemical relationship between the N-amido group and Y may be cis or trans. A trans relationship is preferred.

In formula (1), Y is an oxygen atom or a sulfur atom. Appropriate selection of Y allows for the preparation of oligonucleotide analogs that contain phosphodiester, phosphorothioate and phosphorodithioate linkages, as well as combinations of these internucleotide linkages. Preferably, Y is an oxygen atom. When Y is a sulfur atom it is particularly preferred that $R^1$ is trifluoromethyl and $R^2$, $R^3$ and $R^4$ are hydrogen.

The $R^5$ groups are chosen such that phosphoramidite (I) couples efficiently with a reactive group on the growing oligonucleotide analog chain, e.g., a 5' hydroxyl group, to form a phosphorous(III) internucleotide linkage between phosphoramidite (1) and the oligonucleotide analog chain. The $R^5$ groups are independently selected, i.e., they may be the same or different. Preferable $R^5$ groups are $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms; or both $R^5$ groups together with the nitrogen atom they are bonded to form a $C_2$–$C_8$ heterocycloalkyl group containing up to three heteroatoms, a substituted a $C_2$–$C_8$ heterocycloalkyl group containing up to three heteroatoms, a $C_3$–$C_{11}$ hetaryl group containing up to three heteroatoms or a substituted $C_3$–$C_{11}$ hetaryl group containing up to three heteroatoms. More preferably, the $R^5$ groups are each a $C_1$–$C_8$ alkyl group or together with the nitrogen atom they are bonded to form a $C_2$–$C_8$ heterocycloalkyl group containing up to three heteroatoms. Even more preferably, each $R^5$ group is a branched $C_1$–$C_8$ alkyl group. Most preferably, both $R^5$ groups are isopropyl.

$R^6$ is preferably a labile blocking group. The term "blocking group" refers to a protecting group that may be removed selectively under mild conditions during step-wise assembly of an oligonucleotide analog. The $R^6$ blocking group is preferably chosen such that the conditions required to remove this group will not remove other protecting groups in the oligonucleotide analog, particularly the 2-N-amidoethyl group. More preferably, $R^6$ is an acid-labile blocking group. Many acid-labile groups are suitable for use in oligonucleotide analog synthesis. Preferably, $R^6$ is 4,4'-dimethoxytrityl (DmTr), monomethoxytrityl, diphenylmethyl, phenylxanthen-9-yl (pixyl) or 9-(p-methoxyphenyl)xanthen-9-yl (Mox). The 4,4'-dimethoxytrityl (DmTr) group is particularly preferred.

Phosphoramidite (1) may be a 2' deoxy analog, i.e., X may be hydrogen. Alternatively, phosphoramidite (1) may be substituted at the 2' position. Preferably, the 2' substituents are groups that enhance the hybridization of an oligonucleotide analog with its target nucleic acid, a group that improves the in vivo stability of an oligonucleotide analog or enhances the pharmacokinetic and/or pharamacodynamic properties of an oligonucleotide analog. Examples of 2' substituents, X, in formula (1) include X is selected from the group consisting of hydrogen, hydroxyl, F, Cl, Br, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, substituted $C_4$–$C_{15}$ heterocycloaralkyl containing up to three heteroatoms, O-$C_1$–$C_8$ alkyl, substituted O-$C_1$–$C_8$ alkyl (such as $CF_3$), O-$C_2$–$C_8$ heterocycloalkyl containing up to three heteroatoms, substituted O-$C_2$–$C_8$ heterocycloalkyl containing up to three heteroatoms, O-$C_6$–$C_{14}$ aryl (such as phenyl), substituted O-$C_6$–$C_{14}$ aryl, O-$C_3$–$C_{11}$ hetaryl containing up to three heteroatoms, substituted O-$C_3$–$C_{11}$ hetaryl containing up to three heteroatoms, O-$C_7$–$C_{18}$ aralkyl (such as benzyl), substituted O-$C_7$–$C_{18}$ aralkyl, O-$C_4$–$C_{15}$ heterocycloaralkyl containing up to three heteroatoms, substituted O-$C_4$–$C_{15}$ heterocycloaralkyl containing up to three heteroatoms, O-$C_1$–$C_8$-alkyl-O-$C_1$–$C_8$-alkyl, O-$C_1$–$C_8$ alkenyl, O-$C_1$–$C_8$ alkoxyamino, O-tri-$C_1$–$C_8$-alkyl silyl (such as tert-butyldimethylsilyl), substituted O-tri-$C_1$–$C_8$-alkyl silyl, NH-$C_1$–$C_8$ alkyl, N-($C_1$–$C_8$)$_2$, NH-$C_1$–$C_8$ alkenyl, N-($C_1$–$C_8$)$_2$ alkenyl, S-$C_1$–$C_8$ alkyl, S-$C_1$–$C_8$ alkenyl, $NH_2$, $N_3$, NH-$C_1$–$C_8$-alkyl-$NH_2$, polyalkylamino and an RNA cleaving group. Preferable RNA cleaving groups include the O-{3-propoxy-[2-naphthyl-7-(1-(dimethylaminosulfonyl)-imidazol-4-yl)]} group or the O-{3-propoxy-[2-naphthyl-7-(1-(dimethylaminosulfonyl-2-methoxy-5-acetylaminomethylimidazol-4-yl)]} group. These groups are disclosed by Cook et al, U.S. Pat. No. 5,359,051.

Preferably, the 2' substituents are hydrogen, hydroxyl, O-$C_1$–$C_8$ alkyl, F, O-$C_1$–$C_8$-alkoxyamino or O-$C_1$–$C_8$-alkyl-O-$C_1$–$C_8$-alkyl. More preferably, the 2' substituents are O-$C_1$–$C_8$ alkyl, F or O-$C_1$–$C_8$-alkyl-O-$C_1$–$C_8$-alkyl.

Most preferably, the 2' substituent is hydrogen or a methoxyethoxy group.

The group B represents an unprotected or a protected heterocyclic base. Any natural or non-natural heterocyclic base may be used as B, such as adenine, guanine, cytosine, thymine, uracil, 2-aminopurine, inosine, 5-substituted pyrimidines, e.g., 5-methylcytosine, and 5-nitropyrrole. Other suitable heterocyclic bases are described by Merigan et al., U.S. Pat. No. 3,687,808. Preferably, the heterocyclic base is attached to C-1 of the sugar moiety of nucleoside analog phosphoramidite (1) via a nitrogen of the base.

During oligonucleotide analog synthesis these heterocyclic groups may be protected to prevent any reactive group, e.g., an exocyclic amino group, from participating in undesired side reactions. The term "protected" in reference to oligonucleotide and nucleoside analogs means that reactive moieties such as exocyclic amino groups, 2'-hydroxyl groups, oxygen or sulfur bonded to phosphorus atoms, and the like, have protective groups which are generally removed after synthesis of the oligonucleotide analog is completed. Preferably, these protective groups are labile to a base and/or a nucleophile. This term also includes oligonucleotide and nucleoside analogs which have groups that do not require such protection, e.g., heterocyclic bases such as thymine or abasic nucleosides.

Preferable protecting groups for the heterocyclic bases are base labile groups. The exocyclic amino groups of the heterocyclic bases are preferably protected with acyl groups that are removed by base treatment after synthesis of the oligonucleotide analog. More preferably, these acyl groups have from 2 to 10 carbon atoms. N-benzoyl and N-isobutyryl protecting groups are particularly preferred. Adenine is preferably protected as an $N^2$-isobutyryl derivative. Guanine is preferably protected as an $N^6$-isobutyryl derivative. Cytidine is preferably protected as an $N^4$-benzoyl derivative.

Nucleoside analog phosphoramidite (1) may be prepared using synthetic methodology which is well-known to those of ordinary skill in the art. An amine having the formula $NHR^2$—$CHR^3CHR^4$—YH was coupled with an acid of formula $R^1$—COOH or an activated acid equivalent thereof to the afford corresponding amide of formula (2):
$R^1CONHR^2CHR^3CHR^4$—YH.

Suitable examples of the amine having the formula $NHR^2$—$CHR^3CHR^4$—YH include 2-aminoethanol, N-methyl-N-trifluoroacetyl-trans-2-aminocyclohexanol, ephidrine, 2-N-alkylaminoethanols, 2-N-methylaminoethanol, aminoethanethiol, 2-N-alkylaminoethanethiols and 2-N-methylaminoethanethiol.

The term "activated acid equivalent" refers to the carboxylic acid moiety of $R^1$-COOH that has been chemically activated to facilitate amide formation with the amino group of the amine having the formula $NHR^2$—$CHR^3CHR^4$—YH. Suitable activated acid equivalents include anhydrides, e.g., $R^1COOCOR^1$, acid halides and activated esters. Preferred activated acid equivalents of the formula $R^1$—COOH include trifluoroacetic anhydride, trifluoroacetyl chloride, acetic anhydride, acetyl chloride, and acetyl bromide.

This reaction is preferably performed in an inert solvent. Suitable solvents include hydrocarbons, halocarbons, ethers, amide solvents, dialkylsulfoxides. Examples of inert solvents include p-xylene, toluene, dichloromethane, dichloroethane, diethyl ether, tetrahydrofuran (THF), dimethtlformamide (DMF), dimethylsulfoxide (DMSO) and mixtures thereof. A preferred solvent is p-xylene. This reaction may be conducted at any convenient temperature, preferably from −10 to 50° C. The reaction is more preferably conducted at a temperature between −10 to 20° C.; most preferably between −5° C. to 10° C. A non-nucleophilic base may be used in the coupling reaction, if desired. The base should preferably not react with the acid or activated acid equivalent thereof. Preferred non-nucleophilic bases are pyridine or trialkylamines, e.g., triethylamine.

The alcohol or thiol moiety of amide (2), i.e., —YH, is then reacted with a phosphorous trihalide followed by treatment with an amine of formula $HN(R^5)_2$ to produce the phosphitylating reagent of formula (3):

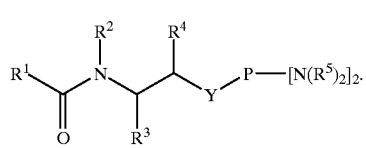

(3)

The preferred phosphorous trihalide is phosphorous trichloride. This reaction is preferably performed in an inert solvent. Suitable solvents include hydrocarbons, halocarbons, ethers and mixtures thereof. Preferable inert solvents are p-xylene, toluene, dichloromethane, dichloroethane, diethyl ether, THF and mixtures thereof. A most preferred solvent is diethyl ether. The reaction may be conducted at any convenient temperature, preferably from −10 to 50° C. The reaction is more preferably conducted at a temperature between −10 to 20° C.; most preferably between −5 to 10° C.

Phosphitylating reagent (3) may be reacted with a protected, i.e., blocked, nucleoside analog of formula (4):

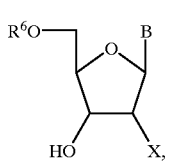

(4)

preferably in the presence of an activator, to produce the inventive nucleoside analog phosphoramidite (1). Suitable activators are well-known in the art and include 1H-tetrazole, 5-(4-nitrophenyl)-1H-tetrazole and diisopropylamino tetrazolide. The preferred activator is 1H-tetrazole. This reaction is preferably conducted in an inert solvent. Preferable inert solvents are hydrocarbons, halocarbons, ethers, nitrites and mixtures thereof. Examples of inert solvents include p-xylene, toluene, dichloromethane, dichloroethane, diethyl ether, THF, acetonitrile and mixtures thereof. Acetonitrile is particularly preferred. The reaction may be conducted at any convenient temperature, preferably from 0 to 50° C. The reaction is more preferably conducted at 5 to 30° C. Room temperature, i.e., 18 to 25° C., is most preferred.

The present invention is also directed to a 2-N-amidoethyl protected dinucleotide analog phosphoramidite of formula (5):

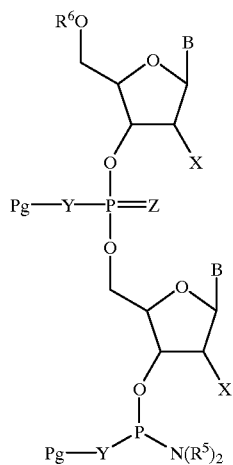

(5)

where
each Pg is independently selected from the group consisting of a 2-N-amidoethyl group having the formula $R^1CONR^2CHR^3CHR^4$—, a group labile to a base and/or a nucleophile and an allyl group, where at least one Pg group in the dinucleotide analog phosphoramidite (5) is a 2-N-amidoethyl group. Preferably, both Pg groups are 2-N-amidoethyl groups.

A variety of other protecting groups for the oxygen and/or sulfur atoms attached to the phosphorus atom in dinucleotide analog phosphoramidite (5) may be used in combination with the 2-N-amidoethyl group. Preferably, these protecting groups are labile to a base and/or a nucleophile. Preferable examples of such protecting groups are β-cyanoethyl, 4-cyano-2-butenyl and 2-diphenylmethylsilylethyl (DPSE).

The 4-cyano-2-butenyl protecting group is removed by d-elimination using the standard $NH_3/H_2O$ deprotection conditions used in the art. 4-cyano-2-butenyl protected nucleoside analog phosphoramidites may be prepared with 4-cyano-2-butene-1-ol and appropriately protected nucleoside analogs using known synthetic methodology. The synthesis of 4-cyano-2-butene-1-ol is described by Ravikumar et al, *Synthetic Communications* 1996, 26(9), 1815-1819.

The 2-diphenylmethylsilylethyl (DPSE) protecting group is described in Ravikumar et al., WO 95/04065. This protecting group may be removed by treatment with a base, preferably aqueous ammonium hydroxide. The DPSE group may also be removed with fluoride ion. Preferably, the fluoride ion is provided from a salt such as a tetraalkylammonium fluoride, e.g., tetrabutylammonium fluoride (TBAF) or an inorganic fluoride salt, e.g., potassium fluoride or cesium fluoride in a solvent such as THF, acetonitrile, dimethoxyethane or water.

An allyl group is also a suitable protecting group for the oxygen and sulfur atoms attached to the phosphorus in the nucleoside analog phosphoramidite and phosphorothioamidite, respectively. The allyl protecting group is described in U.S. Pat No. 5,026,838. The term "allyl group" includes allyl, methallyl, crotyl, prenyl, geranyl, cinnamyl and p-chlorocinnamyl groups. The number of carbon atoms in these groups is preferably 3 to 10. The allyl group may be removed with a palladium(0) compound and a nucleophilic agent, such as an amine or a formic acid salt, under neutral conditions at room temperature. A preferred reagent is tetrakis(triphenylphosphine) palladium(0) and n-butylamine in THF.

Z in formula (5) is an oxygen atom or a sulfur atom. Appropriate choice of Z allows the internucleosidic linkage containing Z to be a phosphodiester, phosphorothioate or phosphorodithioate linkage, depending on selection of Y. For example, when Y and Z are both oxygen the linkage is a phosphodiester. When Y is oxygen and Z is sulfur, or vice versa, the linkage is a phosphorothioate. When Y and Z are both sulfur the linkage is a phosphorodithioate. It is to be understood that the terms phosphodiester, phosphorothioate and phosphorodithioate refer to the internucleotide linkage after removal of the Pg protecting groups.

Dinucleotide analog phosphoramidite (5) may be prepared using well-established synthetic methodology known to those of ordinary skill in the art. First, blocked nucleoside analog phosphoramidite (6) is coupled with protected nucleoside analog (7) to afford a dinucleotide analog of formula (8) containing a phosphorous(III) linkage:

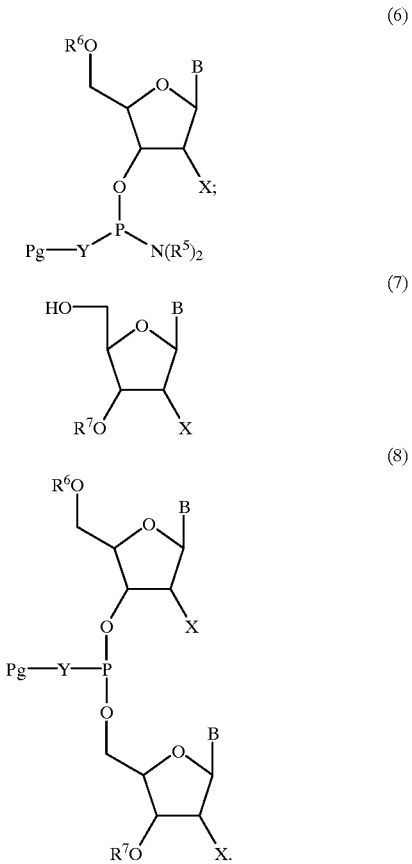

In protected nucleoside analog (7), $R^7$ is a protecting group that prevents the 3' hydroxyl group from participating in any undesired side reactions. $R^7$ is preferably a protecting group that mnay be removed selectively without removing the $R^6$ group or the Pg groups. An $R^7$ group that may be removed under neutral conditions is preferred. An acyl group containing 2 to 10 carbon atoms is more preferred. Most preferably, $R^7$ is a levulinyl group.

The coupling of (6) and (7) to produce dinucleotide analog (8) is preferably conducted in the presence of an activator. Suitable activators are well-known to those of ordinary skill in the art and include 1H-tetrazole, 5-(4-nitrophenyl)-1H-tetrazole and diisopropylamino tetrazolide. The preferred activator is 1H-tetrazole.

The coupling of (6) and (7) is preferably performed in an inert solvent. Suitable solvents include hydrocarbons, halocarbons, ethers, nitrites and mixtures thereof. Preferable inert solvents are p-xylene, toluene, dichloromethane, dichloroethane, diethyl ether, THF, acetonitrile and mixtures thereof. A most preferred solvent is acetonitrile. The reaction may be conducted at any convenient temperature, preferably from 0 to 50° C. The reaction is more preferably conducted at 5 to 30° C. Room temperature, i.e., 18 to 25° C., is most preferred.

The phosphorous(III) linkage in dinucleotide analog (8) may be oxidized or sulfurized to produce the corresponding dinucleotide analog (9) containing an oxidized or sulfurized phosphorous(V) linkage:

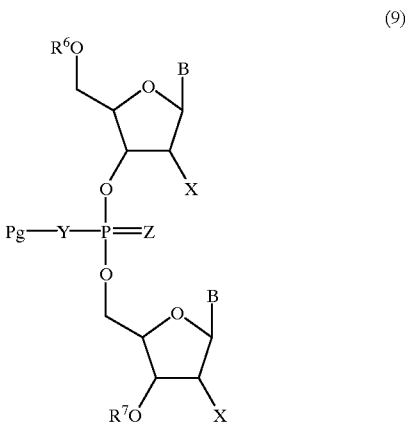

where Z is an oxygen atom or a sulfur atom.

The phosphorous(III) linkage in (8) may be oxidized with variety of oxidizing agents known to those of ordinary skill in the art. Suitable oxidizing agents include $I_2/THF/H_2O$, $H_2O_2/H_2O$, tert-butyl hydroperoxide or a peracid, such as m-chloroperbenzoic acid. The oxidation reaction is preferably conducted in an inert solvent. Preferred inert solvents are THF and $H_2O$. Oxidation may be conducted at any convenient temperature, preferably between at 5 to 50° C. Room temperature, i.e., 18 to 25° C., is particularly preferred.

Alternatively, the phosphorous(III) linkage in (8) may be sulfurized with a variety of sulfurizing reagents known in the art. Suitable sulfurizing reagents include elemental sulfur in carbon disulfide, see for example, U.S. Pat. No. 5,252,723 and U.S. Pat. No. 5,449,769; the Beaucage reagent, 3H-1,2-benzodithiol-3-one, see for example, U.S. Pat. No. 5,003,097; tetraethylthiuram disulfide, see for example, U.S. Pat. No. 5,166,387; phenylacetyl disulfide see for example, *Recherches Travaux Chimigues des Pays-Bas* 1991, 110, 325–331; *Tetrahedron Letters* 1989, 30, 6757–6760; *Synthesis* 1981, 637–638.

Another sulfurizing reagent that may be used is a thiodicarbonic acid diester polysulfide having the formula

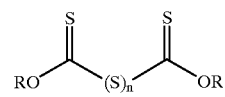

where n is 2, 3 or 4, and each R is an inert side chain. These groups preferably do not contain any reactive moieties which may lead to side reactions and poor yields in the sulfurization reaction. Preferably, each R is independently $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, or substituted $C_4$–$C_{15}$ heterocycloaralkyl containing up to three heteroatoms. More preferably, each R is independently $C_2$–$C_8$ alkyl, $C_6$–$C_{14}$ aryl or substituted $C_6$–$C_{14}$ aryl. Most preferably, each R is independently ethyl or p-chlorophenyl.

The thiodicarbonic acid diester polysulfide is preferably delivered to the oligonucleotide analog in a suitable organic solvent, such as acetonitrile, pyridine, THF, dichloromethane, dichloroethane and collidine. These solvents may be used singly or as mixtures in any proportion. Preferred solvents are pyridine, dichloromethane and mixtures thereof. Pyridine is most preferred. The reagent may be used an any effective concentration for sulfurizing a phosphorous(III) linkage, preferably from 0.01 M to 1.5 M, more preferably from 0.2 to 1.2 M; and most preferably from 0.5 to 1.0 M.

The sulfurization reaction may be conducted at any convenient temperature in the range, preferably from 0 to 70° C.; more preferably from 10 to 40° C.; and most preferably at room temperature, i.e., 18 to 25° C The sulfurization reaction is preferably conducted for 30 seconds to 15 minutes; more preferably, 1 to 15 minutes; and most preferably, 3 to 10 minutes. Preferably, sulfurization is performed under anhydrous conditions with the exclusion of air. The thiodicarbonic acid diester polysulfide is described in the commonly assigned application U.S. patent application Ser. No. 08/811,232 (Title: Reagent Useful for Synthesizing Sulfurized Oligonuclotide Analogs, now U.S. Pat. No. 5.783,690).

Following oxidation or sulfurization, the $R^7$ group in dinucleotide analog (9) may be removed to produce a dinucleotide analog of formula (10) containing a free 3' hydroxyl group:

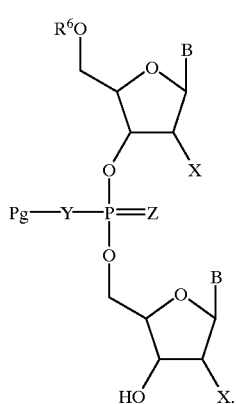

(10)

Removing the $R^7$ group, thereby deprotecting the 3' hydroxyl group, is preferably accomplished by treating dinucleotide analog (9) under conditions suitable to remove the $R^7$ group without removing the $R^6$ and Pg groups. When $R^7$ is a levulinyl group, deprotection may be effected by treating dinucleotide analog (10) with hydrazine hydrate in a 1:1 mixture of pyridine and acetic acid. The reaction is preferably conducted at a temperature of 5 to 30° C. Room temperature, i.e., 18 to 25° C., is particularly preferred.

Following removal of the $R^7$ group, dinucleotide analog (10) may be reacted with a phosphitylating reagent having the formula Pg—Y—P—$[N(R^5)_2]_2$ to produce dinucleotide analog phosphoramidite (5). In this coupling reaction an activator is preferably used. Suitable activators are well-known to those of ordinary skill in the art and include 1H-tetrazole, 5-(4-nitrophenyl)-1H-tetrazole and diisopropylamino tetrazolide. The preferred activator is 1H-tetrazole. This reaction is preferably performed in an inert solvent. Suitable solvents include hydrocarbons, halocarbons, ethers, nitrites and mixtures thereof. Preferable inert solvents are p-xylene, toluene, dichloromethane, dichloroethane, diethyl ether, THF, acetonitrile and mixtures thereof. A most preferred solvent is acetonitrile. The reaction may be conducted at any convenient temperature, preferably from 0 to 50° C.; more preferably at 5 to 30° C. Room temperature, i.e., 18 to 25° C., is most preferred.

As noted above, at least one Pg group in dinucleotide analog phosphoramidite (5) is a 2-N-amidoethyl group. The 2-N-amidoethyl group may be derived from nucleoside analog phosphoramidite (6) and/or the phosphitylating reagent having the formula Pg—Y—P—$[N(R^5)_2]_2$. Preferably, both Pg groups are 2-N-amidoethyl groups.

Dinucleotide analog phosphoramidite (5) is a useful reagent in the blockmer approach to the synthesis of oligonucleotide analogs. Individual blocks of different sequence may be prepared, e.g. A-A, A-G, A-C, A-T, etc. The blocks may then be used for step-wise synthesis of oligonucleotide analogs using solution or solid phase synthetic techniques.

The present invention is also directed to a 2-N-amidoethyl protected oligonucleotide analog having the formula (11):

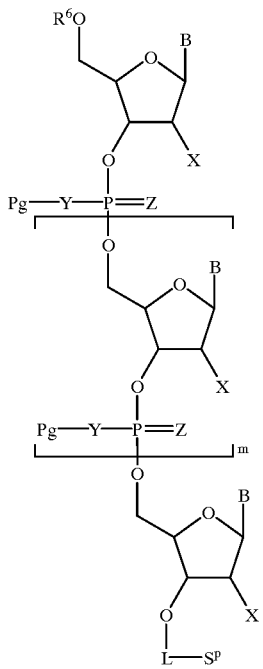

(11)

where

L is a group labile to a base and/or a nucleophile;

$S^p$ is a solid support; and m is 0 or a positive integer.

The protected oligonucleotide analog (11) may have any combination of Pg groups, provided that at least one Pg group is a 2-N-amidoethyl group. Preferably, all of the Pg groups are 2-N-amidoethyl groups. Other suitable Pg groups are described above.

Oligonucleotide analog (11) may have oxidized and/or sulfurized internucleosidic linkages, i.e., Z may be an oxygen atom or a sulfur atom, as described above.

The 2-amidoethyl protected oligonucleotide analog of formula (11) is attached to a solid support, S^P, by a linker group, L, at the terminal 3' hydroxyl group. It is preferable that L be selected to be easily cleaved when synthesis is complete in order to release the oligonucleotide analog from the solid support. Preferably, L is a group that may be cleaved upon exposure to a base and/or a nucleophile. More preferably, L is an acyl group and most preferably, L is a carboxyl group esterifed with the terminal 3' hydroxyl group of the oligonucleotide analog.

Suitable solid supports include controlled pore glass (CPG); oxalyl-controlled pore glass (Alul et al, *Nucleic Acids Research* 1991, 19, 1527); TENTAGEL support, see Wright et al, *Tetrahedron Letters* 1993, 34, 3373; POROS, a polystyrene resin available from PERCEPTIVE BIOSYSTEMS; and a polystyrene/divinylbenzene copolymer. Controlled pore glass is the most preferred solid support.

Oligonucleotide analog (11) may have a length of 2 to 200 monomer units, i.e., m in formula (11) may be 0 to 198. Preferably, the oligonucleotide analog contains 2 to 100 monomer units, i.e., m may be 0 to 98; more preferably, from 2 to 50 monomer units, i.e., m may be 0 to 48; and most preferably from 2 to 25 monomer units, i.e., m may be 0 to 23. The ranges for m include all subranges therebetween.

The 2-N-amidoethyl protected oligonucleotide analog of formula (11) is preferably synthesized using solid phase techniques well-known to those of ordinary skill in the art. Preferably oligonucleotide analog (11) is synthesized by solid phase methods using a automated DNA synthesizer, i.e., an APPLIED BIOSYSTEMS model 380B or a similar machine. Detailed procedures for synthesizing oligonucleotide analogs using nucleotide analog phosphoramidites are described in the following references: M. J. Gait (ed.), *Oligonucleotide Synthesis, A Practical Approach* (ILR Press, 1984); J. S. Cohen (ed.), *Oligonucleotides: Antisense Inhibitors of Gene Expression*, (CRC Press, Inc., Boca Raton, Fla., 1989).

Generally, the synthetic approach may involve the following steps: (1) deprotecting a blocked reactive functionality on the growing oligonucleotide analog chain, or on the first nucleoside analog monomer, to form a deblocked reactive functionality; (2) reacting an appropriately blocked and protected nucleoside analog phosphoramidite or phosphorthioamidite monomer with the deblocked reactive functionality of the growing nucleotide analog chain to form a phosphorus(III) linkage; (3) capping any unreacted functionality or reactive groups; and (4) oxidizing or sulfurizing the newly-formed phosphorus(III) linkage to obtain the phosphorus atom in an oxidized or sulfurized pentacoordinate state. The sequential addition of nucleoside analog phosphoramidites and/or phosphorothioamidites is repeated until an oligonucleotide analog having the desired sequence length is obtained.

A capping step may be used after each coupling reaction to permanently block all uncoupled reactive functionalities. Suitable capping reagents are well-known to those of ordinary skill in the art. A preferred capping reagent is acetic anhydride/lutidine/THF (1:1:8) with N-methylimidazole/THF.

In a preferred embodiment, the 2-N-amidoethyl protected oligonucleotide analog (11) is synthesized by a method containing the steps:

(a) deblocking a blocked 5' hydroxyl group of a protected nucleoside analog of formula (12) attached to a solid support:

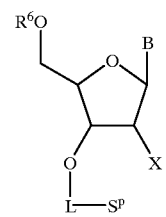

(12)

to produce a nucleoside analog attached to a solid support having a free 5' hydroxyl group;

(b) reacting the free 5' hydroxyl group with a nucleoside analog phosphoramidite of formula (6) having a blocked 5' hydroxyl group, to produce an oligonucleotide analog containing a phosphorous(III) linkage and a blocked 5' hydroxyl group;

(c) reacting the phosphorous(III) linkage with an oxidizing agent or a sulfurizing reagent to produce an oligonucleotide analog of formula (11);

(d) deblocking the blocked 5' hydroxyl group; and (e) repeating steps (b) through (d) at least once followed by repeating steps (b) and (c).

After step-wise synthesis as described above, the 2-N-amidoethyl protected oligonucleotide analog (11) may be simultaneously deprotected and removed from the solid support to produce a deprotected oligonucleotide analog of formula (13):

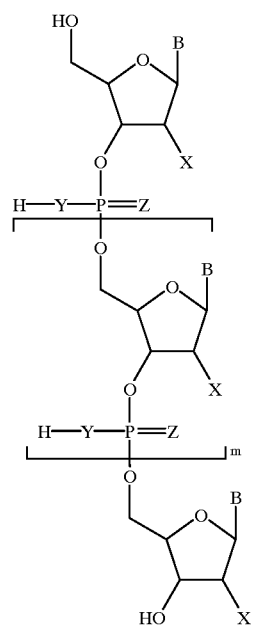

(13)

where B, X, Y, Z and m are as defined above.

The simultaneous deprotection and removal of 2-N-amidoethyl protected oligonucleotide analog (11) to produce oligonucleotide analog (13) is preferably accomplished in aqueous ammonium hydroxide at a temperature between room temperature, i.e., 18 to 25° C., and 75° C.; more preferably, between room temperature and 65° C.; and most preferably, between room temperature and 60° C. A temperature of 55° C. is particularly preferred. The deprotection reaction time is preferably 1 to 30 hours; more preferably, 1 to 24 hours; and most preferably, 12–24 hours. The concentration of ammonium hydroxide in the solution used for deprotection is preferably 20 to 30% by weight; more preferably, 25 to 30% by weight; and most preferably, 28 to 30% by weight.

It is to be appreciated that each internucleotide linkage in the oligonucleotide analog (12) may be ionized, depending on the pH, temperature and salt conditions. Each internucleotide linkage will be ionized in aqueous solution at physiologic pH, temperature and salt conditions, i.e., pH 7.2, 37° C. and about 150 mM monovalent salts.

Having generally described this invention, a further understanding may be obtained by reference to certain specific examples which are provided herein for purposes of illustration only and are not intended to be limiting unless otherwise specified.

EXAMPLES

Example 1

N-Methyl-N-trifluoroacetylaminoethanol

Trifluoroacetic acid (10 ml; 129 mmol) was added to a stirred solution of N-methylaminoethanol (9.72 g; 129 mmol) in p-xylene (10 ml) at 0° C. The mixture was heated under reflux for 12 hours, then allowed to cool and stand at room temperature overnight. All the volatiles were removed and the product distilled under high vacuum to afford the product as a clear liquid. Yield 9.8 g (44%); b.p. 110° C./1 mm.

Example 2

N-methyl-N-trifluoroacetylaminoethyl N,N-diisopropylphosphordiamidite

A 500 mL three-necked flask equipped with a magnetic stirrer, a glass stopper and an inlet for argon was assembled under argon atmosphere. All glassware was dried in an oven at 120° C. for 1 hour. The reaction flask was charged with anhydrous ether (150 mL) and phosphorous trichloride (9.27 g; 67.5 mmol). N-Methyl-N-trifluoroacetylaminoethanol (50 mmol) in ether (50 mL) was added to the reaction flask slowly with stirring at 0° C. (ice cooling) using a pressure-equalized addition funnel. After addition was complete, the ice bath was removed and the reaction was stirred for three hours. The reaction mixture was then transferred to a 500 mL flask and concentrated under reduced pressure.

To this colorless product in anhydrous ether (200 mL) was added diisopropylamine (57.7 mL) at 0° C. under argon. After the addition was complete, stirring was continued at room temperature for 16 hours (overnight). The reaction mixture was filtered and concentrated to afford a colorless viscous liquid.

Example 3

Protected N-methyl-N-trifluoroacetylaminoethyl Phosphoramidite Monomers

A. 5'-O-(4,4'-dimethoxytrityl)thymidine-3'-O-(2-N-methyl-N-trifluoroacetylaminoethyl N,N-diisopropyl-phosphoramidite)

A 250 mL two-necked flask equipped with a magnetic stirrer, a gas inlet for argon, and a septum was assembled under an argon atmosphere. All glassware had been dried at 120° C. for 1 hour. The flask was charged with 5'-O-(4,4'-dimethoxytrityl)thymidine (CHEM-IMPEX; 3.81 g; 7 mmol) and 1H-tetrazole (CHEM-IMPEX; 5.6 mmol). Anhydrous acetonitrile (50 mL) was added. To this stirred mixture under argon at room temperature was added a solution of N-methyl-N-trifluoroacetylaminoethyl N,N-diisopropyl-phosphordiamidite (10.5 mmol) in acetonitrile (50 mL). After stirring for two hours, thin layer chromatography on WHATMAN Silica Gel 60A Diamond KGF (100% ethyl acetate) showed disappearance of the starting nucleoside. The reaction mixture was filtered and the filtrate diluted with ethyl acetate (100 mL), washed once with cold saturated sodium bicarbonate solution, brine and then dried ($MgSO_4$). The dried solution was concentrated under reduced pressure to afford a viscous foamy liquid. The crude product was purified by flash chromatography using silica gel. A gradient solvent system of ethyl acetate and hexane was used. Triethylamine (1%) was used throughout the purification. The fractions corresponding to the product were combined and concentrated to afford a solid (78%). $^{31}P$ NMR ($CDCl_3$) showed two signals at δ 145.483, 146.176 corresponding to two diastereomeric products.

B. $N^2$-Isobutyryl-5'-O-(4,4'-dimethoxytrityl)-2'-deoxyguanosine-3'-O-(2-N-methyl-N-trifluoroacetylaminoethyl N,N-diisopropylphosphoramidite)

A 250 mL two-necked flask equipped with a magnetic stirrer, a gas inlet for argon, and a septum was assembled under an argon atmosphere. All glassware was dried at 120° C. for 1 hour. The flask was charged with $N^2$-isobutyryl-5'-O-(4,4'-dimethoxytrityl)2'-deoxyguanosine (CHEM-IMPEX; 3.195 g; 5 mmol) and 1H-tetrazole (4 mmol). Anhydrous acetonitrile (50 mL) was added. To this stirred mixture under argon at room temperature was added a solution of N-methyl-N-trifluoroacetylaminoethyl N,N-diisopropylphosphordiamidite (7.5 mmol) in acetonitrile (50 mL). After stirring for two hours, thin layer chromatography on WHATMAN Silica Gel 60A Diamond KGF (100% ethyl acetate) showed disappearance of starting nucleoside. The reaction mixture was filtered and the filtrate diluted with ethyl acetate (100 mL), washed once with cold saturated sodium bicarbonate solution, brine and dried ($MgSO_4$). The dried solution was concentrated under reduced pressure to afford a viscous foamy liquid. The crude product was purified by flash chromatography using silica gel. A gradient solvent system consisting of ethyl acetate and hexane was used. Triethylamine (1%) was used throughout the purification. The fractions corresponding to the product were combined and concentrated to afford the product as a glass (75%).

C. $N^6$-Benzoyl-5'-O-(4,4'-dimethoxytrityl)-2'-deoxyadenosine-3'-O-(2-N-methyl-N-trifluoroacetylaminoethyl N,N-diisopropylphosphoramidite)

A 250 mL two-necked flask equipped with a magnetic stirrer, a gas inlet for argon, and a septum was assembled under an argon atmosphere. All glassware was dried at 120° C. for 1 hour. The flask is charged with $N^6$-benzoyl-5'-O-(4,4'-dimethoxytrityl)2'-deoxyadenosine (CHEM-IMPEX; 3.285 g; 5 mmol) and 1H-tetrazole (4 mmol). Anhydrous acetonitrile (50 mL) was added. To this stirred mixture under argon at room temperature was added a solution of N-methyl-N-trifluoroacetylaminoethyl N,N-diisopropylphosphordiamidite (6 mmol) in acetonitrile (50 mL). After stirring for two hours, the reaction mixture was filtered and concentrated to afford a viscous foamy material. The crude product was purified by flash chromatography using silica gel. A gradient solvent system consisting of ethyl acetate and hexane was used. Triethylamine (1%) was used throughout the purification. The fractions corresponding to the product were combined and concentrated to afford a viscous foamy liquid (68%). $^{31}$P NMR (CDCl$_3$) showed two signals at δ 146.1, 146.478 corresponding to two diastereomeric products.

D. N$^4$-Benzoyl-5'-O-(4,4'-dimethoxytrityl)-2'-deoxycytidine-3'-O-(2-N-methyl-N-trifluoroacetylaminoethyl N,N-diisopropylphosphoramidite)

A 250 mL two-necked flask equipped with a magnetic stirrer, a gas inlet for argon, and a septum was assembled under an argon atmosphere. All glassware was dried at 120° C. for 1 hour. The flask was charged with N$^4$-benzoyl-5'-O-(4,4'-dimethoxytrityl)2'-deoxycytidine (CHEM-IMPEX; 3.169 g; 5 mmol) and 1H-tetrazole (4 mmol). Anhydrous acetonitrile (50 mL) was added. To this stirred mixture under argon at room temperature was added a solution of N-methyl-Ntrifluoroacetylaminoethyl N,N-diisopropylphosphordiamidite (7.5 mmol) in acetonitrile (50 mL). After stirring for two hours, thin layer chromatography on WHATMAN Silica Gel 60A Diamond KGF (100% ethyl acetate) showed disappearance of starting nucleoside. The reaction mixture was filtered and the filtrate diluted with ethyl acetate (100 mL), washed once with cold saturated sodium bicarbonate solution, brine and dried (MgSo$_4$). The dried solution was concentrated under reduced pressure to afford a viscous foamy liquid. The crude product was purified by flash chromatography using silica gel. A gradient solvent system consisting of ethyl acetate and hexane was used. Triethylamine (1%) is used throughout the purification. The fractions corresponding to the product were combined and concentrated to afford a solid (74%).

Example 4

Synthesis of a T-T Phosphorothioate Dimer 100 milligrams (4 mmole) of 5'-O-dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with dichloromethane and then with acetonitrile. Then, a 0.2 M solution of 5'-O-(4, 4'dimethoxytrityl)thymidine-3'-O-(2-N-methyl-N-trifluoroacetylaminoethyl N,N-diisopropylphosphoramidite) in acetonitrile and a 0.4 M solution of 1H-tetrazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8) and N-methylimidazole/THF was added to cap the unreacted 5'-hydroxyl group. The product was washed with acetonitrile.

The carrier containing the compound was treated with 30% aqueous ammonium hydroxide solution for 90 minutes. The aqueous solution was filtered and concentrated under reduced pressure to afford a phosphorothioate dimer of T-T.

Example 5

Synthesis of a C-T Phosphorothioate Dimer 100 milligrams (4 mmole) of 5'-O-dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of N$^4$-benzoyl-5'-O-(4,4'-dimethoxytrityl)-2'deoxycytidine-3'-O-(2-N-methyl-N-trifluoroacetylaminoethyl N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes and then incubated at 55° C. for 12 hours. The aqueous solution was filtered, concentrated under reduced pressure to afford the phosphorothioate dimer of dC-T.

Example 6

Synthesis of a T-T Phosphodiester Dimer 100 milligrams (4 mmole) of 5'-O-dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product is washed with dichloromethane and then with acetonitrile. Then, a 0.2 M solution of 5'-O-(4, 4'dimethoxytrityl)thymidine-3'-O-(2-N-methyl-N-trifluoroacetylaminoethyl N, N-diisopropylphosphoramidite) in acetonitrile and a 0.4M solution of 1H-tetrazole in acetonitrile was added, and reacted at room temperature for 5 minutes. The product was washed with acetonitrile, and then a 0.1 M iodine solution in water/pyridine/THF (2/20/80) was added and reacted at room temperature for 5 minutes. The support was washed with acetonitrile and then a solution of acetic anhydride/ lutidine/THF (1:1:8) and N-methylimidazole/THF was added to cap the unreacted 5'-hydroxyl group. The product was washed with acetonitrile.

The carrier containing the compound was treated with 30% aqueous ammonium hydroxide solution for 90 minutes at room temperature and then incubated at 55° C. for 1 hour. The aqueous solution was filtered, concentrated under reduced pressure to afford T-T phosphodiester dimer.

Example 7

Synthesis of a 5'-TTTTTTT-3' Phosphorothioate Heptamer 50 milligrams (2 mmole) of 5'-O-dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of 5'-O-( 4,4'-dimethoxytrityl)thymidine-3'-O-(2-N-methyl-N-trifluoroacetylaminoethyl N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methylimidazole/THF was added to cap the unreacted 5'-hydroxyl group. The product was washed with acetonitrile.

This complete cycle was repeated five more times to afford the completely protected thymidine heptamer. The carrier containing the compound was treated with 30% aqueous ammonium hydroxide solution for 90 minutes at room temperature and then incubated at 55° C. for 1 hour. The aqueous solution was filtered and concentrated under reduced pressure to afford a phosphorothioate heptamer of TTTTTTT.

Example 8

Synthesis of a 5'-d(GACTT)-3' Phosphorothioate Pentamer 50 milligrams (2 mmole) of 5'-O-dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of 5'-O-(4,4'-dimethoxytrityl)thymidine-3'-O-(2-N-methyl-N-trifluoroacetylaminoethyl N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8) and N-methyl imidazole/THF was added to cap the unreacted 5'-hydroxyl group. The product was washed with acetonitrile.

A dichloromethane solution of 2% dichloroacetic acid (volume/volume) was added to deprotect the 5'-hydroxyl group. The product was washed with acetonitrile. Then, a 0.2 M solution of $N^4$-benzoyl-5'-O-(4,4'-dimethoxytrityl)-2'-deoxycytidine-3'-O-(2-N-methyl-N-trifluoroacetylaminoethyl N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8) and N-methyl imidazole/THF was added to cap the unreacted 5'-hydroxyl group. The product was washed with acetonitrile.

A dichloromethane solution of 2% dichloroacetic acid (volume/volume) was added to deprotect the 5'-hydroxyl group. The product was washed with acetonitrile. Then, a 0.2 M solution of $N^6$-benzoyl-5'-O-(4,4'-dimethoxytrityl)-2'-deoxyadenosine-3'-O-(2-N-methyl-N-trifluoroacetylaminoethyl N,N-diisopropylphosphoramidite) in anhydrous acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methylimidazole/THF was added to cap the unreacted 5'-hydroxyl group. The product was washed with acetonitrile.

A dichloromethane solution of 2% dichloroacetic acid (volume/volume) was added to deprotect the 5'-hydroxyl group. The product was washed with acetonitrile. Then, a 0.2 M solution of $N^2$-isobutyryl-5'-O-(4,4'-dimethoxytrityl)-2'-deoxyguanosine-3-(2-N-methyl-N-trifluoroacetylaminoethyl N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8) and N-methylimidazole/THF was added to cap the unreacted 5'-hydroxyl group. The product was washed with acetonitrile.

The carrier containing the compound was treated with 30% aqueous ammonium hydroxide solution for 90 minutes at room temperature and then incubated at 55° C. for 24 hours. The aqueous solution was filtered and concentrated under reduced pressure to give a phosphorothioate tetramer of 5'-dG-dA-dC-T3'.

Example 9

N-Methyl-N-trifluoroacetyl-trans-aminocyclohexanol

Methylchloroformate (2 equiv.) was added to NaHCO$_3$ (1 equiv.) and trans-2-aminocyclohexanol (1 equiv.) in CH$_2$Cl$_2$ at 0° C. After the addition, the reaction was allowed to warm to room temperature. When the recaction was complete, the reaction mixture was filtered and concentrated to afford N-methylformate-trans-2-aminocyclohexanol. This compound was dissolved in anhydrous THF and treated with lithium aluminum hydride (2 equiv.) to afford N-methyl-trans-2-aminocyclohexanol.

Trifluoroacetic acid was added to N-methyl-trans-aminocyclohexanol (1 equiv.) in p-xylene at 0° C. The mixture was heated under reflux for 12 hours and then allowed to cool and stand at room temperature overnight. All the volatiles were removed and the product was distilled under high vacuum to afford N-methyl-trifluoroacetyl-trans-2-aminocyclohexanol.

All references cited in the present application are hereby incorporated by reference in their entirety.

Obviously, numerous modifications and variations of the present invention are possible in light of the above teachings. It is therefore to be understood that within the scope of the appended claims, the invention can be practiced otherwise than as specifically described herein.

What is claimed as new and desired to be secured by Letters: Patent of the United States is:

1. A nucleotide analog comprising a phosphorous(III) group represented by the formula:

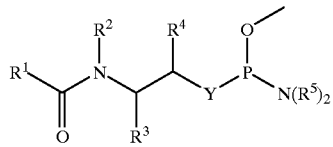

wherein

R$^1$ is selected from the group consisting of C$_1$–C$_8$ alkyl, substituted C$_1$–C$_8$ alkyl, C$_2$–C$_8$ heterocycloalkyl containing up to three heteroatoms, substituted C$_2$–C$_8$ heterocycloalkyl containing up to three heteroatoms, C$_6$–C$_{14}$ aryl, substituted C$_6$–C$_{14}$ aryl, C$_3$–C$_{11}$ hetaryl containing up to three heteroatoms, substituted C$_3$–C$_{11}$ hetaryl containing up to three heteroatoms, C$_7$–C$_{18}$ aralkyl, substituted C$_7$–C$_{18}$ aralkyl, C$_4$–C$_{15}$ heterocycloaralkyl containing up to three heteroatoms and substituted C$_4$–C$_{15}$ heterocycloaralkyl containing up to three heteroatoms;

R$^2$, R$^3$ and R$^4$ are independently selected from the group consisting of hydrogen, C–C$_8$ alkyl, substituted C$_1$–C$_8$ alkyl, C$_2$–C$_8$ heterocycloalkyl containing up to three heteroatoms, substituted C$_2$–C$_8$ heterocycloalkyl containing up to three heteroatoms, C$_6$–C$_{14}$ aryl, substituted C$_6$–C$_{14}$ aryl, C$_3$–C$_{11}$ hetaryl containing up to three heteroatoms, substituted C$_3$–C$_{11}$ hetaryl containing up to three heteroatoms, C$_7$–C$_{18}$ aralkyl, substituted C$_7$–C$_{18}$ aralkyl, C$_4$–C$_{15}$ heterocycloaralkyl containing up to three heteroatoms and substituted C$_4$–C$_{15}$ heterocycloaralkyl containing up to three heteroatoms, or R$^3$ and R$^4$ together with the carbon atoms they are bonded to form a C$_3$–C$_8$ cycloalkyl group, a substituted C$_3$–C$_8$ cycloalkyl group, a C$_2$–C$_8$ heterocycloalkyl group containing up to three heteroatoms, a substituted C$_2$–C$_8$ heterocycloalkyl group containing up to three heteroatoms, a C$_6$–C$_{14}$ aryl group, a substituted C$_6$–C$_{14}$ aryl group, a C$_3$–C$_{11}$ hetaryl group containing up to three heteroatoms, a substituted C$_3$–C$_{11}$ hetaryl group containing up to three heteroatoms;

each R$^5$ is independently selected from the group consisting of C$_1$–C$_8$ alkyl, substituted C$_1$–C$_8$ alkyl, C$_2$–C$_8$ heterocycloalkyl containing up to three heteroatoms, substituted C$_2$–C$_8$ heterocycloalkyl containing up to three heteroatoms, C$_6$–C$_{14}$ aryl, substituted C$_6$–C$_{14}$ aryl, C$_3$–C$_{11}$ hetaryl containing up to three heteroatoms, substituted C$_3$–C$_{11}$ hetaryl containing up to three heteroatoms, C$_7$–C$_{18}$ aralkyl, substituted C$_7$–C$_{18}$ aralkyl, C$_4$–C$_{15}$ heterocycloaralkyl containing up to three heteroatoms, and substituted C$_4$–C$_{15}$ heterocycloaraikyl containing up to three heteroatoms; or both R$^5$ groups together with the nitrogen atom they are bonded to form a member selected from the group consisting of a C$_2$–C$_8$ heterocycloalkyl group containing up to three heteroatoms, a substituted a C$_2$–C$_8$ heterocycloalkyl group containing up to three heteroatoms, a C$_3$–C$_{11}$ hetaryl group containing up to three heteroatoms and a substituted C$_3$–C$_{11}$ hetaryl group containing up to three heteroatoms; and Y is oxygen or sulfur.

2. The nucleotide analog of claim 1, wherein

R$^1$ is selected from the group consisting of C$_1$–C$_8$ alkyl, substituted C$_1$–C$_8$ alkyl, C$_2$–C$_8$ heterocycloalkyl containing up to three heteroatoms, substituted C$_2$–C$_8$ heterocycloalkyl containing up to three heteroatoms, C$_6$–C$_{14}$ aryl, substituted C$_6$–C$_{14}$ aryl, C$_3$–C$_{11}$ hetaryl containing up to three heteroatoms and substituted C$_3$–C$_{11}$ hetaryl containing up to three heteroatoms;

R$^2$ and R$^3$ are independently selected from the group consisting of hydrogen and C$_1$–C$_8$ alkyl; and R$^4$ is selected from the group consisting of hydrogen, C$_6$–C$_{14}$ aryl, substituted C$_6$–C$_{14}$ aryl, C$_3$–C$_{11}$ hetaryl containing up to three heteroatoms and substituted C$_3$–C$_{11}$ hetaryl containing up to three heteroatoms; or R$^3$ and R$^4$ together with the carbon atoms they are bonded to form a C$_3$–C$_8$ cycloalkyl group or a substituted C$_3$–C$_8$ cycloalkyl group.

3. The nucleotide analog of claim 2, wherein

R$^1$ is selected from the group consisting of methyl, fluoromethyl, difluoromethyl, trifluoromethyl and phenyl.

4. The nucleotide analog of claim 2, wherein R$^2$ and R$^3$ are independently selected from the group consisting of hydrogen and methyl.

5. The nucleotide analog of claim 2, wherein R$^4$ is selected from the group consisting of hydrogen, C$_6$–C$_{14}$ aryl and C$_3$–C$_{11}$ hetaryl containing up to three heteroatoms; or R$^3$ and R$^4$ together with the carbon atoms they are bonded to form a C$_5$–C$_6$ cycloalkyl group or a substituted C$_5$–C$_6$ cycloalkyl group.

6. The nucleotide analog of claim 1, wherein

R$^1$ is selected from the group consisting of methyl, fluoromethyl, difluoromethyl, trifluoromethyl and phenyl;

R$^2$ and R$^3$ are independently selected from the group consisting of hydrogen and methyl; and R$^4$ is selected from the group consisting of hydrogen, C$_6$–C$_{14}$ aryl and C$_3$–C$_{11}$ hetaryl containing up to three heteroatoms; or R$^3$ and R$^4$ together with the carbon atoms they are bonded to form a C$_5$–C$_6$ cycloalkyl group or a substituted C$_5$–C$_6$ cycloalkyl group.

7. The nucleotide analog of claim 1, which contains a group represented by the formula:

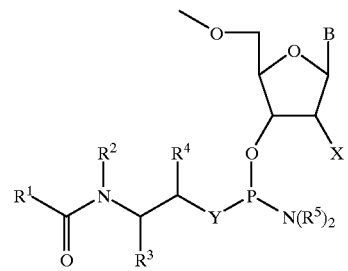

wherein

R$^1$, R$^2$, R$^3$, R$^4$, R$^5$ and Y are as defined above;

B is a protected or unprotected heterocyclic base; and

X is selected from the group consisting of hydrogen, hydroxyl, F, Cl, Br, C$_1$–C$_8$ alkyl, substituted C$_1$–C$_8$ alkyl, C$_2$–C$_8$ heterocycloalkyl containing up to three heteroatoms, substituted C$_2$–C$_8$ heterocycloaikyl containing up to three heteroatoms, C$_6$–C$_{14}$ aryl, substituted C$_6$–C$_{14}$ aryl, C$_3$–C$_{11}$ hetaryl containing up to three heteroatoms, substituted C$_3$–C$_{11}$ hetaryl containing up to three heteroatoms, C$_7$–C$_{18}$ aralkyl, substituted $C_7-C_{18}$ aralkyl, $C_4-C_{15}$ heterocycloaralkyl containing up to three heteroatoms, substituted $C_4-C_{15}$ heterocycloaralkyl containing up to three heteroatoms, O-$C_1-C_8$ alkyl, substituted O-$C_1-C_8$ alkyl, O-$C_2-C_8$ heterocycloalkyl containing up to three heteroatoms, substituted O-$C_2-C_8$ heterocycloalkyl containing up to three heteroatoms, O-$C_6-C_{14}$ aryl, substituted O-$C_6-C_{14}$ aryl, O-$C_3-C_{11}$ hetaryl containing up to three heteroatoms, substituted O-$C_3-C_{11}$ hetaryl containing up to three heteroatoms, O-$C_7-C_{18}$ aralkyl, substituted O-$C_7-C_{18}$ aralkyl, O-$C_4-C_{15}$ heterocycloaralkyl containing up to three heteroatoms, substituted O-$C_4-C_{15}$ heterocycloaralkyl containing up to three heteroatoms, O-$C_1-C_8$-alkyl-O-$C_1-C_8$ alkyl, O-$C_1-C_8$ alkenyl, O-$C_1-C_8$ alkoxyarnino, O-tri-$C_1-C_8$-alkyl silyl, substituted O-tri-$C_1-C_8$-alkyl silyl, NH-$C_1-C_8$ alkyl, N-$(C_1-C_8)_2$, NH-$C-C_8$ alkenyl, N-$(C_1-C_8)_2$ alkenyl, S-$C_1-C_8$ alkyl, S-$C_1-C_8$ alkenyl, $NH_2$, $N_3$, NH-$C_1-C_8$-alkyl-$NH_2$, polyalkylamino and an RNA cleaving group.

8. The nucleotide analog of claim 1, wherein
$R^1$ is selected from the group consisting of methyl, fluoromethyl, difluoromethyl, trifluoromethyl and phenyl;
$R^2$ and $R^3$ are independently selected from the group consisting of hydrogen and methyl; and
$R^4$ is selected from the group consisting of hydrogen, $C_6-C_{14}$ aryl and $C_3-C_{11}$ hetaryl containing up to three heteroatoms; or
$R^3$ and $R^4$ together with the carbon atoms they are bonded to form a $C_5-C_6$ cycloalkyl group or a substituted $C_5-C_6$ cycloalkyl group.

9. The nucleotide analog of claim 8, wherein X is hydrogen.

10. The nucleotide analog of claim 8, wherein B is selected from the group consisting of adenine, guanine, cytosine, thymine, uracil, 2-aminopurine, inosine and 5-methylcytosine, wherein the exocyclic amino group of the base is optionally protected with an acyl group.

11. The nucleotide analog of claim 1, which contains 2 to 25 nucleotide units.

12. A nucleotide analog unit comprising a phosphorous (V) group represented by the formula:

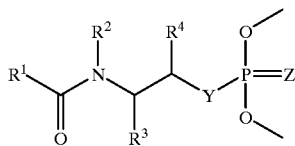

wherein
$R^1$ is selected from the group consisting of $C_1-C_8$ allyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms, substituted $C_3-C_{11}$ hetaryl containing up to three heteroatoms, $C_7-C_{18}$ aralkyl, substituted $C_7-C_{18}$ aralkyl, $C_4-C_{15}$ heterocycloaralkyl containing up to three heteroatoms and substituted $C_4-C_{15}$ heterocycloaralkyl containing up to three heteroatoms;
$R^2$, $R^3$ and $R^4$ are independently selected from the group consisting of hydrogen, $C_1-C_8$ alkyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms, substituted $C_3-C_{11}$ hetaryl containing up to three heteroatoms, $C_7-C_{18}$ aralkyl, substituted $C_7-C_{18}$ araLkyl, $C_4-C_{15}$ heterocycloaralkyl containing up to three heteroatoms and substituted $C_4-C_{15}$ heterocycloaralkyl containing up to three heteroatoms, or
$R^3$ and $R^4$ together with the carbon atoms they are bonded to form a $C_3-C_8$ cycloalkyl group, a substituted $C_3-C_8$ cycloalkyl group, a $C_2-C_8$ heterocycloalkyl group containing up to three heteroatoms, a substituted $C_2-C_8$ heterocycloalkyl group containing up to three heteroatoms, a $C_6-C_{14}$ aryl group, a substituted $C_6-C_{14}$ aryl group, a $C_3-C_{11}$ hetaryl group containing up to three heteroatoms, a substituted $C_3-C_{11}$ hetaryl group containing up to three heteroatoms;
each $R^5$ is independently selected from the group consisting of $C_1-C_8$ alkyl, substituted $C_1-C_8$ alky, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3C_{11}$ hetaryl containing up to three heteroatoms, substituted $C_3-C_{11}$ hetaryl containing up to three heteroatoms, $C_7-C_{18}$ aralkyl, substituted $C_7-C_{18}$ aralkyl, $C_4-C_{15}$ heterocycloaralkyl containing up to three heteroatoms, and substituted $C_4-C_{15}$ heterocycloaralkyl containing up to three heteroatoms; or both $R^5$ groups together with the nitrogen atom they are bonded to form a member selected from the group consisting of a $C_2-C_8$ heterocycloalkyl group containing up to three heteroatoms, a substituted a $C_2-C_8$ heterocycloalkyl group containing up to three heteroatoms, a $C_3-C_{11}$ hetaryl group containing up to three heteroatoms and a substituted $C_3-C_{11}$ hetaryl group containing up to three heteroatoms;
Y is oxygen or sulfur; and
Z is oxygen or sulfur.

13. The nucleotide analog of claim 12, wherein
$R^1$ is selected from the group consisting of $C_1-C_8$ alkyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms and substituted $C_3-C_{11}$ hetaryl containing up to three heteroatoms;
$R^2$ and $R^3$ are independently selected from the group consisting of hydrogen and $C_1-C_8$ alkyl; and
$R^4$ is selected from the group consisting of hydrogen, $C_6-C_{14}$ aryl, substituted $C_6-C_{14}$ ary, $C_3-C_{11}$ hetaryl containing up to three heteroatoms and substituted $C_3-C_{11}$ hetaryl containing up to three heteroatoms; or
$R^3$ and $R^4$ together with the carbon atoms they are bonded to form a $C_3-C_8$ cycloalkyl group or a substituted $C_3-C_8$ cycloalkyl group.

14. The nucleotide analog of claim 13, wherein
$R^1$ is selected from the group consisting of methyl, fluoromethyl, difluoromethyl, trifluoromethyl and phenyl.

15. The nucleotide analog of claim 13, wherein $R^2$ and $R^3$ are independently selected from the group consisting of hydrogen and metlhyl.

16. The nucleotide analog of claim 13, wherein $R^4$ is selected from the group consisting of hydrogen, $C_6-C_{14}$ aryl and $C_3-C_{11}$ hetaryl containing up to three heteroatoms; or
$R^3$ and $R^4$ together with the carbon atoms they are bonded to form a $C_5-C_6$ cycloalkyl group or a substituted $C_5-C_6$ cycloalkyl group.

17. The nucleotide analog of claim 13, wherein $R^1$ is selected from the group consisting of methyl, fluoromethyl, difluoromethyl, trifluoromethyl and phenyl;

$R^2$ and $R^3$ are independently selected from the group consisting of hydrogen and methyl; and $R^4$ is selected from the group consisting of hydrogen, $C_6$–$C_{14}$ aryl and $C_3$–$C_{11}$ hetaryl containing up to three heteroatoms; or $R^3$ and $R^4$ together with the carbon atoms they are bonded to form a $C_5$–$C_6$ cycloalkyl group or a substituted $C_5$–$C_6$ cycloalkyl group.

18. The nucleotide analog of claim 12, which contains a group represented by the formula:

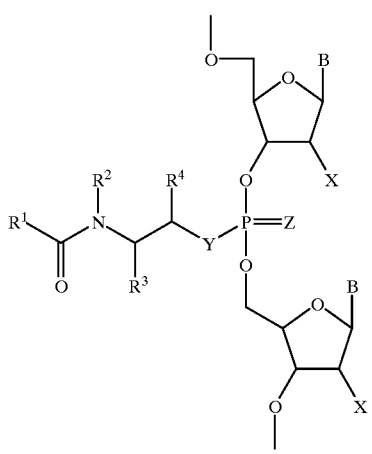

wherein $R^1$, $R^2$, $R^3$, $R^4$, $R^5$, Y and Z are as defined above;

each B is a protected or unprotected heterocyclic base; and each X is independently selected from the group consisting of hydrogen, hydroxyl, F, Cl, Br, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, substituted $C_4$–$C_{15}$ heterocycloaralkyl containing up to three heteroatoms, O-$C_1$–$C_8$ alkyl, substituted O-$C_1$–$C_8$ alkyl, O-$C_2$–$C_8$ heterocycloalkyl containing up to three heteroatoms, substituted O-$C_2$–$C_8$ heterocycloalkyl containing up to three heteroatoms, O-$C_6$–$C_{14}$ aryl, substituted O-$C_6$–$C_{14}$ aryl, O-$C_3$–$C_{11}$ hetaryl containing up to three heteroatoms, substituted O-$C_3$–$C_{11}$ hetaryl containing up to three heteroatoms, O-$C_7$–$C_{18}$ aralkyl, substituted O-$C_7$–$C_{18}$ aralkyl, O-$C_4$–$C_{15}$ heterocycloaralkyl containing up to three heteroatoms, substituted O-$C_4$–$C_{15}$ heterocycloaralkyl containing up to three heteroatoms, O-$C_1$–$C_8$-alkyl-O-$C_1$–$C_8$-alkyl, O-$C_1$–$C_8$ alkenyl, O-$C_1$–$C_8$ alkoxyamino, O-tri-$C_1$–$C_8$-alkyl silyl, substituted O-tri-$C_1$–$C_8$-alkyl silyl, NH-$C_1$–$C_8$ alkyl, N-($C_1$–$C_8$)$_2$, NH-$C_1$–$C_8$ alkenyl, N-($C_1$–$C_8$)$_2$ alkenyl, S-$C_1$–$C_8$ alkyl, S-$C_1$–$C_8$ alkenyl, $NH_2$, $N_3$, NH-$C_1$–$C_8$-alkyl-$NH_2$, polyalkylamino and an RNA cleaving group.

19. The nucleotide analog of claim 18, wherein $R^1$ is selected from the group consisting of methyl, fluoromethyl, difluoromethyl, trifluoromethyl and phenyl;

$R^2$ and $R^3$ are independently selected from the group consisting of hydrogen and methyl; and $R^4$ is selected from the group consisting of hydrogen, $C_6$–$C_{14}$ aryl and $C_3$–$C_{11}$ hetaryl containing up to three heteroatoms; or $R^3$ and $R^4$ together with the carbon atoms they are bonded to form a $C_5$–$C_6$ cycloalkyl group or a substituted $C_5$–$C_6$ cycloalkyl group.

20. The nucleotide analog of claim 18, wherein each X is hydrogen.

21. The nucleotide analog of claim 18, wherein each B is independently selected from the group consisting of adenine, guanine, cytosine, thymine, uracil, 2-aminopurine, inosine and 5-methylcytosine, where the exocyclic amino group of each base is optionally protected with an acyl group.

22. The nucleotide analog of claim 18, which contains 2 to 25 nucleotide units.

* * * * *